(12) United States Patent
Jordan, IV et al.

(10) Patent No.: US 7,316,994 B2
(45) Date of Patent: Jan. 8, 2008

(54) PERFUME POLYMERIC PARTICLES

(75) Inventors: Glenn Thomas Jordan, IV, Indian Springs, OH (US); Bernard William Kluesener, Harrison, OH (US); Mark Robert Sivik, Mason, OH (US); Vicente Santamarina, Loveland, OH (US); Robert Richard Dykstra, Cleves, OH (US); Nathalia Lebedev, Maineville, OH (US); Lois Sara Gallon, Finneytown, OH (US); Ellen Schmidt Baker, Cincinnati, OH (US); Patrick Amrhein, Hochheim (DE); Dieter Boeckh, Limburgerhof (DE); Stefan Frenzel, Manheim (DE); Ekkehard Jahns, Weinheim (DE); Volker Schwendemann, Neustadt (DE)

(73) Assignee: The Procter & Gamble Company, Cincinnati, OH (US)

( * ) Notice: Subject to any disclaimer, the term of this patent is extended or adjusted under 35 U.S.C. 154(b) by 231 days.

(21) Appl. No.: 10/695,282

(22) Filed: Oct. 28, 2003

(65) Prior Publication Data

US 2004/0110648 A1 Jun. 10, 2004

Related U.S. Application Data

(60) Provisional application No. 60/423,107, filed on Nov. 1, 2002.

(51) Int. Cl.
*C11D 3/37* (2006.01)

(52) U.S. Cl. .................... 510/475; 510/527

(58) Field of Classification Search ............. 510/475, 510/527
See application file for complete search history.

(56) References Cited

U.S. PATENT DOCUMENTS

| 3,577,518 | A | 5/1971 | Shepherd et al. |
| 3,946,749 | A | 3/1976 | Papantoniou et al. |
| 4,326,967 | A | 4/1982 | Melville |
| 4,394,127 | A | 7/1983 | Melville |
| 5,246,603 | A | 9/1993 | Tsaur et al. |
| 6,024,943 | A | 2/2000 | Ness et al. |
| 6,194,375 | B1 | 2/2001 | Ness et al. |
| 6,849,591 | B1 * | 2/2005 | Boeckh et al. ............ 510/475 |
| 7,125,835 | B2 * | 10/2006 | Bennett et al. ............ 512/4 |
| 2002/0010107 | A1 | 1/2002 | Hoshino et al. |
| 2002/0065208 | A1 | 5/2002 | Aubay et al. |
| 2003/0158072 | A1 * | 8/2003 | Goodson et al. ........... 510/439 |

FOREIGN PATENT DOCUMENTS

| EP | 0 617 051 A3 | 9/1994 |
| EP | 0 950 070 B1 | 7/1998 |
| EP | 0 925 776 A2 | 6/1999 |
| EP | 1 160 311 A1 | 5/2001 |
| EP | 1 146 057 A1 | 10/2001 |
| JP | 63 122796 | 5/1988 |
| WO | WO 98/28339 A1 | 7/1998 |
| WO | WO 98/28396 A1 | 7/1998 |
| WO | WO 98/28398 A1 | 7/1998 |
| WO | WO 99/38944 A1 | 8/1999 |
| WO | WO 00/68352 A1 | 11/2000 |
| WO | WO 01/04257 * | 1/2001 |
| WO | WO 01/36577 A1 | 5/2001 |
| WO | WO 01/79303 A1 | 10/2001 |
| WO | WO 02/04586 A1 | 1/2002 |
| WO | WO 02/38713 A1 | 5/2002 |
| WO | WO 02/050230 | 6/2002 |
| WO | WO 2004/041232 A1 * | 5/2004 |

* cited by examiner

*Primary Examiner*—John R. Hardee
(74) *Attorney, Agent, or Firm*—Kim William Zerby; Steven W Miller

(57) ABSTRACT

Perfume polymeric particles, polymeric particles having affinities for certain perfume raw materials, compositions containing them and methods for making the same are provided.

8 Claims, No Drawings

PERFUME POLYMERIC PARTICLES

CROSS REFERENCE TO RELATED APPLICATIONS

This application claims priority under 35 U.S.C. §119(e) from Provisional Application Ser. No. 60/423,107, filed on Nov. 1, 2002.

FIELD OF THE INVENTION

The present invention relates to perfume polymeric particles, which are useful as delivery systems for perfume raw materials. The present invention also relates to compositions comprising the perfume polymeric particles and methods of making the same.

BACKGROUND OF THE INVENTION

In many consumer products, it is desirable for perfume, especially perfume raw materials ("PRMs") to be released slowly over time. Since the most volatile perfume raw materials, referred to as "top notes" are responsible for the "fresh smelling" consumers experience, it is desirable for the more volatile top notes to be released in a controlled and sustained manner. Moreover, top notes are often lost due to evaporation and/or dissolution in aqueous media.

One challenge for the formulators is to minimize the loss of top notes by exploring technologies that enhance the deposition of top notes on substrates, especially in the presence of water or when the substrate is subsequently exposed to water or moisture. Another challenge for the formulators is to control and extend the release of the deposited top notes so that the fresh smelling scent is not exhausted in a short burst.

Some recent developments to meet those challenges are directed to polymerizing the perfume, especially the perfume raw materials, into a polymeric particle; details of these developments are described in WO 01/79303 and EP 925,776. Other developments are directed to absorbing perfume into polymeric particles; details of these developments are described in U.S. Pat. No. 6,149,375; WO 00/68352; WO 98/28398 and WO 98/28339. These developments have failed to teach a polymeric particle that selectively absorbs/adsorbs top notes.

Accordingly, there is a need for perfume polymeric particles that selectively absorb/adsorb PRMs and efficiently deliver the PRMs to a substrate. Moreover, there is a need for perfume polymeric particles having a higher affinity for PRMs such that the amount of PRMs available for delivery to the substrate and for subsequent release is increased. There is a further need that such perfume polymeric particles, once deposited onto a substrate, provide a controlled, sustained release of the PRMs, especially the volatile top notes, over an extended period of time. There is also a need for compositions comprising such perfume polymeric particles such that the amount of PRMs remain with the perfume polymeric particles through the wash, rinse and drying is increased. Additionally, processes for making such perfume polymeric particles and compositions containing them are also needed.

SUMMARY OF THE INVENTION

One embodiment of the present invention relates to a perfume polymeric particle comprising: a polymer; and a perfume comprising a perfume raw material having a Kovats Index value of from about 1000 to about 1400, and optionally one or more of the following characteristics: a molecular weight of less than about 200; a boiling point of less than about 250° C.; a ClogP of less than about 3; wherein the Response factor (RF) of the perfume polymeric particle is at least about 1.5, as measured by the Longevity Test Protocol I or II.

Another embodiment of the present invention relates to a perfume polymeric particle comprising: a polymer and a perfume comprising more than one LKI perfume raw materials, each having a Kovats Index value of from about 1000 to about 1400, and the LKI perfume raw materials collectively provide a first Average Response Factor ($ARF_{LKI}$); and more than one HKI perfume raw materials, each having a Kovats Index value of greater than about 1700, and the HKI perfume raw materials collectively provide a second Average Response Factor ($ARF_{HKI}$); wherein the perfume polymeric particle exhibits a ratio of $ARF_{LKI}/ARF_{HKI}$ of at least about 1.2, as measured by the Longevity Test Protocol I or II.

The present invention also relates to the polymeric particles, the compositions comprising the perfume polymeric particles according to the above embodiments, and methods for making the perfume polymeric particles.

DETAILED DESCRIPTION OF THE INVENTION

Definitions:

"Non-polymerically associated" as used herein means that the perfume is absorbed in, adsorbed on, or otherwise associated with the polymeric particle after the polymeric particle has been formed. In other words, the perfume is not present during polymerization or melting of the polymeric particle. Specifically, the perfume is mixed with preformed polymeric particles to produce a perfume polymeric particle in accordance with the present invention. For purposes of the present invention, the association between the perfume and the polymeric particle excludes encapsulation, which means a polymer almost completely surrounds a perfume in a core-shell type structure.

"Longevity" is indicated by an enhancement and/or increase in the amount of perfume raw material that is released from a substrate at any time point following contact with a benefit agent delivery system.

"Benefit agent delivery system" as used herein refers to a perfume composition comprising a perfume raw material, a polymeric particle and optionally, an adjunct ingredient, combined in such a manner as to increase or enhance the deposition of perfume raw material onto a substrate and/or the release of perfume raw material from a substrate at any time point after said substrate has been exposed to said benefit agent delivery system.

Perfume

Perfumes or perfume oils comprise perfume raw materials ("PRMs") as well as other less volatile materials. PRMs are characterized by their boiling point (B.P.), their octanol/water partitioning coefficient (P), and their Kovats Index values.

The boiling points of many perfume ingredients are reported in, e.g., "Perfume and Flavor Chemicals (Aroma Chemicals)," Steffen Arctander, published by the author, 1969.

The octanol/water partitioning coefficient of a material is the ratio between its equilibrium concentrations in octanol and in water. The octanol/water partitioning coefficient can alternatively be reported on a base 10 logarithmic scale, as logP, and when the calculated value is reported, as ClogP. The perfume ingredients suitable for use in this invention typically have logP of less than about 3.

The logP of many perfume ingredients has been reported; for example, the Pomona92 database, available from Daylight Chemical Information Systems, Inc. (Daylight CIS), Irvine, Calif., contains many, along with citations to the original literature. However, the logP values are most conveniently calculated by the "CLOGP" program, also available from Daylight CIS. This program also lists experimental logP values when they are available in the Pomona92 database. The "calculated logP" (ClogP) is determined by the fragment approach of Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990). The fragment approach is based on the chemical structure of each perfume ingredient, and takes into account the numbers and types of atoms, the atom connectivity, and chemical bonding. The ClogP values, which are the most reliable and widely used estimates for this physicochemical property, are preferably used instead of the experimental logP values in the selection of perfume ingredients which are useful in the present invention.

The Kovats Retention Index system is an accurate method for reporting gas chromatographic (GC) data for interlaboratory substance identification. It is used for eliminating the effects of instrument parameters on the correlations between the retention time and the chemical identification by GC. The Kovats Index (KI or I) value of many perfume ingredients has been reported. The Kovats Index value of an unknown substance can be calculated from the following equation:

$$I = 100\left[n + (N-n)\frac{\log t'_r(\text{unknown}) - \log t'_r(n)}{\log t'_r(N) - \log t'_r(n)}\right]$$

where n is the number of carbon atoms in the smaller alkane
N is the number of carbon atoms in the larger alkane
$t'_r(n)$ is the adjusted retention time of the smaller alkane
$t'_r(N)$ is the adjusted retention time of the larger alkane It is noted that this equation applies to a particular stationary phase in the GC column. Based on the above equation, the Kovats Index for a linear alkane equal to 100 times the number of carbon atoms. For example, octane has a KI value of 800, and decane would have a KI value of 1000. In another example, octanol has a KI value of 826, on a particular phase and hexadecanol would have a KI value of 1626. The KI value used herein are determined using polydimethylsiloxane as the non-polar stationary phase in the column (referred to as a "DB-5 column").

Representative PRMs are identified in the KI Table described herein.

| PRM | KI Value | CAS # | MW |
|---|---|---|---|
| Very Low KI (VLKI) | | | |
| ethyl acetate | 604 | 141-78-6 | 88.1 |
| methyl-2-methylpropanoate | 685 | 547-63-7 | 102.1 |
| 3-hydroxy-2-butanone | 718 | 513-86-0 | 88.1 |
| 1-hexen-3-ol | 789 | 4798-44-1 | 100.1 |
| propyl propanoate | 812 | 106-36-5 | 116.1 |
| ethyl 2-me butyrate | 849 | 7452-79-1 | 130.1 |
| (Z)-3-hexen-1-ol | 858 | 928-96-1 | 100.1 |
| propyl butyrate | 898 | 105-66-8 | 130.1 |
| alpha-Pinene | 937 | 80-56-8 | 136.1 |
| Low KI (LKI) | | | |
| beta-Pinene | 1002 | 127-91-3 | 136.1 |
| Limonene | 1033 | 138-86-3 | 136.1 |
| benzyl alcohol | 1037 | 100-51-6 | 108.1 |
| Melonal | 1055 | 106-72-9 | 140.1 |
| dihydromyrcenol | 1072 | 18479-58-8 | 156.2 |
| methyl benzoate | 1081 | 93-58-3 | 136.1 |
| Linalool | 1100 | 78-70-6 | 154.1 |
| Ligustral | 1090, 1119 | 68039-49-6 | 138.1 |
| methyl cinnamate | 1113 | 103-26-4 | 162.1 |
| phenyl ethyl alcohol | 1122 | 60-12-8 | 122.1 |
| Citronellal | 1155 | 106-23-0 | 154.1 |
| benzyl acetate | 1164 | 140-11-4 | 150.1 |
| l-carvone | 1227 | 6485-40-1 | 150.1 |
| Citronellol | 1237 | 106-22-9 | 156.2 |
| Citral | 1254 | 5392-40-5 | 152.1 |
| anisic aldehyde | 1271 | 123-11-5 | 136.2 |
| Geraniol | 1275 | 106-24-1 | 154.1 |
| ethyl benzoate | 1300 | 93-89-0 | 150.1 |
| methyl anthranilate | 1359 | 134-20-3 | 151.2 |
| Eugenol | 1364 | 97-53-0 | 164.1 |
| beta damascenone | 1386 | 23726-93-4 | 190.1 |
| delta-damascone | 1394 | 71048-82-3 | 192.2 |
| Medium KI (MKI) | | | |
| Vanillin | 1410 | 121-33-5 | 152.0 |
| alpha-ionone | 1425 | 127-41-3 | 192.2 |
| flor acetate | 1443 | 2500-83-6 | 192 |
| Gamma ionone | 1445 | 79-76-5 | 192.2 |
| Geranyl propionate | 1476 | 105-91-9 | 210.2 |
| beta-ionone | 1493 | 14901-07-6 | 192.2 |
| sandalore | 1512 | 065113-99-7 | 210.2 |
| Geranyl acetate | 1577 | 105-87-3 | 196.1 |
| helional | 1589 | 1205-17-0 | 192.1 |
| High KI (HKI) | | | |
| methyl-(E)-cinnamate | 1700 | 1754-62-7 | 162.1 |
| Iso E Super | 1703 | 54464-57-2 | 234.2 |
| hexyl salicylate | 1713 | 6259-76-3 | 222.1 |
| delta dodecalactone | 1713 | 713-95-1 | 198.2 |
| nonanoic acid | 1762 | 112-05-0 | 158.1 |
| hexyl cinnamic aldehyde | 1770 | 101-86-0 | 216.2 |
| benzyl benzoate | 1791 | 120-51-4 | 212.1 |
| cedryl acetate | 1811 | 77-54-3 | 264.2 |
| Ambrox | 1812 | 100679-85-4 | 236.2 |
| exaltolide | 1876 | 106-02-5 | 240.2 |
| phenyl ethyl benzoate | 1887 | 94-47-3 | 226.2 |
| galaxolide | 1893 | 1222-05-5 | 258.2 |
| exaltenone | 1901 | 14595-54-1 | 222.2 |
| isoeugenol | 1902 | 97-54-1 | 164.1 |
| benzyl salicylate | 1904 | 118-58-1 | 228.1 |
| phenyl ethyl phenyl acetate | 1945 | 102-20-5 | 240.1 |
| musk C14/Zenolide | 1959 | 54982-83-1 | 256.2 |
| geranyl benzoate | 1985 | 100012-96-0 | 258.2 |
| phenyl ethyl salicylate | 1987 | 87-22-9 | 242.1 |
| (E,E)-farnesol | 2002 | 106-28-5 | 222.2 |
| ethylene brassylate | 2060 | 105-95-3 | 270.2 |
| tetradecanol | 2116 | 4706-81-4 | 214.2 |
| Phytol | 2128 | 7541-49-3 | 296.5 |
| acetovanillone | 2292 | 498-02-2 | 166.1 |

For the purpose of this invention and the test protocols described herein, low KI PRMs refers to PRMs having Kovats Index value between 1000 and 1400, and high KI PRMs refers to PRMs having Kovats Index value greater than 1700.

The perfume associated with the polymeric particle of the present invention comprises PRMs having one or more of the following characteristics: a molecular weight of less than about 200, a boiling point less than about 250° C. (measured at the normal, standard pressure), a ClogP of less than about 3, or a Kovats Index value of less than about 1700. Such PRMs are often referred to as the "top notes".

Nonlimiting examples of PRMs suitable for use herein include, but are not limited to, benzaldehyde, benzyl acetate, laevo-carvone, geraniol, hydroxycitronellal, cis-jasmone, linalool, nerol, phenyl ethyl alcohol, alpha-terpineol, eugenol, iso-eugenol, indole, methyl cinnamate, methyl-N-methyl anthranilate, vanillin, iso-bornyl acetate, carvacrol, alpha-citronellol, citronellol, anisic aldehyde, linalyl acetate, methyl anthranilate, flor acetate and dihydro myrcenol.

In one embodiment, the PRMs are selected from the group consisting of: benzaldehyde, benzyl acetate, laevo-carvone, geraniol, hydroxycitronellal, cis-jasmone, linalool, nerol, phenyl ethyl alcohol, alpha-terpineol, dihydro myrcenol, citronellol, anisic aldehyde, linalyl acetate, methyl anthranilate, flor acetate and mixtures thereof.

Protocol I Perfume Deposition & Delivery Test

The perfume polymeric particles useful in the perfume compositions of the present invention encompass perfume polymeric particles that enhance/increase the level of perfume raw materials deposited onto and/or released from a substrate.

For purposes of determining if the perfume polymeric particles enhance/increase deposition onto and/or release from a substrate, the following test protocols are provided. A fabric article in an aqueous medium is used as the substrate for purposes of these test protocols. The following test protocols can be used to determine if a perfume polymeric particle falls within the scope of the present invention. A perfume polymeric particle falls outside the scope of the present invention when all of the following test protocols indicate so.

Protocol IA (Perfume Accord Delivery or Longevity Test): Each benefit agent delivery system that comprises a perfume raw material and a polymeric particle is tested in accordance with Protocol IA. Each perfume raw material (PRM) commonly found in a perfume is tested with each polymeric particle (PP) to determine if the combination (PRM-PP) demonstrates an enhancement and/or increase in the level of PRM delivered and/or a longevity that is greater than that obtained for the PRM alone.

Multiple PRMs, such as those available in a commercial perfume accord, may be tested together in the presence of single or multiple polymeric particles (PPs), as long as the analytical measurements (such as chromatography) are not compromised by such combination.

For example, a PRM delivery system that contains three PRMs, and a single polymeric particle ($PP^1$) requires the following single-variable test: the Sample, which contains $PRM^1$-$PP^1$, $PRM^2$-$PP^1$ and $PRM^3$-$PP^1$, is compared with the Control, which contains $PRM^1$, $PRM^2$ and $PRM^3$, provided that said PRMs are chromatographically separable such that the amount of each PRM can be determined in the presence of the other. Perfume raw materials that are not chromatographically separable from one another must be run in separate tests.

In another example where $PRM^1$ and $PRM^3$ are not separable, then one of the following tests is required:
 I. sample ($PRM^1$-$PP^1$ and $PRM^2$-$PP^1$) vs. control ($PRM^1$ and $PRM^2$), and sample ($PRM^3$-$PP^1$) vs. control ($PRM^3$); or
 II. sample ($PRM^2$-$PP^1$ and $PRM^3$-$PP^1$) vs. control ($PRM^2$ and $PRM^3$), and sample ($PRM^1$-$PP^1$) vs. control ($PRM^1$); or
 III. sample ($PRM^1$-$PP^1$) vs. control ($PRM^1$), sample ($PRM^2$-$PP^1$) vs. control ($PRM^2$), and sample ($PRM^3$-$PP^1$) vs. control ($PRM^3$).

The PRM in any test should not be present at a concentration much greater than the concentration of another PRM in the same test such that the results are affected (i.e., causing the results to be significantly different than when the PRMs are tested separately). Typically, when the concentrations of the PRMs are within a factor of about 10, the results do not appear to be affected by the presence of other PRMs in the same test. If test results appear to be affected, separate tests for the PRMs are required.

(a) Sample Concentration

The concentrations of PRMs and PP to be used in the Longevity Test (LT) are the lowest concentrations, in a series of solutions prepared from an initial test solution ($TS_0$), at which each PRM in the test solution is detected in the headspace sample collected from the treated substrate at one or more of the designated time points. If this condition is not met by $TS_0$, the concentrations of PRMs and PP in the test solution are doubled and the new solution ($TS_1$) is tested in the same manner. The process is repeated until the above PRM detection condition is met. The concentrations of PRMs and PP in the test solution ($TS_n$) that meets the above PRM detection condition relate to the concentrations of the PRMs and PP in $TS_0$ according to the following equation:

$$[PRM, PP] \text{ in } TS_n = 2^n [PRM, PP] \text{ in } TS_0; \text{ where } n=0, 1, 2, 3 \ldots$$

In some instances, the process of doubling the concentration is repeated until the concentration of the PRMs and of PP both exceed 5% by weight of the test solution and the above PRM detection condition is still not met. Then, the following alternatives may be used in conducting the test. The aliquot of $TS_n$ transferred onto the substrate is increased from 1.0 mL to 3 mL, then to 10 mL, or the substrate size is increased to 1.0 g, 3. g, then to 10 g, until (i) the above PRM detection condition is met, or (ii) with respect to individual PRM that has a concentration greater than 0.1 wt % of the perfume, at least one of the following two alternative conditions is met:
 (1) at least 80% of the low KI PRMs in the test solution and at least 80% of high KI PRMs in the test solution are detected in the headspace sample collected from the treated substrate at one or more of the designated time points; or
 (2) at least 10 of the low KI PRMs in the test solution and at least 5 of the high KI PRMs in the test solution are detected in the headspace sample collected from the treated substrate at one or more of the designated time points.

(b) The Test Procedure

The test solution is prepared by dissolving or mixing PRM(s) and PP(s) that are to be tested together into a composition at concentrations equal to those used in a consumer product, such as a laundry detergent. For example, the respective concentration of PRM(s) and PP(s) in a consumer product may be 2.0% and 4.0% by weight of the product. The solution is closed to the atmosphere and aged for 24 hours at room temperature to obtain the initial test solution, designated $TS_0$.

A 4 cm diameter fabric circle, weighing 0.45 to 0.65 g, is cut from an 86/14 cotton/poly terry wash cloth (obtained from EMC, 7616 Reinfold Drive, Cincinnati, Ohio 45237) and used as the test substrate. The weights of substrates in a given test should be within ±0.02 g of one another. A 1.0 mL aliquot of $TS_0$ is transferred by a pipette onto the substrate, with the pipette pointing close to the center of the substrate. Then, a 1.0 mL aliquot of deionized (DI) water is added to the substrate in the same manner. The substrate is lathered by rubbing against the palm of a nitrile-gloved hand for 1 minute. The substrate is then placed in a bottle containing 40 mL of 35° C. DI water; the bottle is capped and shaken for 30 seconds. The substrate is then removed using forceps and gently blotted on paper towels to remove excess water. The substrate, treated by the above steps (including charging with test solution, diluting, lathering/washing and rinsing) is left open to the atmosphere under ambient conditions to air dry for the specified period of time. Subsequently, the substrate is analyzed via headspace gas chromatography (HSGC) to determine the amount of each perfume raw material in the headspace at each of the following times: 2, 6 and 24 hours.

(c) Headspace Gas Chromatography (HSGC)

A suitable equipment is described by S. Maeno and P. A. Rodriguez in J. Chromatography, vol. A731 (1996) pages 201-215. The equipment includes:

1) a headspace collector to contain the substrate (treated and air dried as described above) and allow PRM(s) to partition into the headspace and reach equilibrium;

2) a trap containing a porous polymer, which has the ability to retain aroma materials (such as perfume or perfume raw materials);

3) a transfer device to transfer the trapped headspace vapors onto a GC for quantitative analysis; and 4) GC-MS with headspace detection capabilities, and uses helium as the mobile phase.

A substrate, which has been treated and air dried for a specified time period as described above, is placed in a headspace collector and allowed to partition and reach equilibrium, which takes about two hours. After equilibration, a trap containing a porous polymer having the ability to retain aroma materials, preferably Tenax® TA 35/60 mesh (available from Gerstel, Inc., Baltimore, Md.), is operatively connected to the headspace collector to capture the equilibrated headspace vapors. A transfer device is used to transfer the trapped headspace vapors, which contains perfume raw materials, onto a GC for quantitative analysis. This device is able to heat the porous polymer trap containing the collected headspace vapors, and transfer the vapors to a cold trap cooled to lower than about −100° C. (generally by liquid nitrogen). Following complete transfer to the cold trap, the cold trap is flash heated in a short period of time, typically about 1 minute, to a temperature of about 280° C., resulting in the transfer of the headspace vapors directly onto a capillary GC column.

A typical column is a 30-60 meters long with an inner diameter of 0.18-0.32 mm, with a stationary phase, which can be, 100% dimethylpolysiloxane (a DB-5 column) or phenylmethylpolysiloxane containing about 5% phenyl. The GC-MS has the capability of identifying and quantifying PRMs of the aldehyde- or ketone-type. Identification is accomplished via Mass Spectrometry and quantification is performed using a separate detector, such as an FID (flame ionization) detector or PID (photo ionization) detector. Specific GC/MS conditions are described below.

The perfume components are separated on a DB-5 column (dimethylsiloxane, 60 m×0.32 mm, 0.25 μm) in split mode to both an MS (for identification) and FID (for quantitation).

GC conditions are as following: the sample is held at oven temperature of about 35° C. for 2 min, then the GC is programmed to ramp up to 200° C. at 4° C./min, followed by a ramp to 325° C. at 10° C./min. Inlet pressure is kept constant at 13.7 psi (9.45 N/m$^2$), which is equivalent to an inert gas (e.g., helium) flow of about 2.4 mL/min. MS conditions are as following: scan range 35 to 400 amu (atomic units). Transfer line is maintained at about 250° C.

The quantitative measurements should be reproducible to within 20% of the average from the runs. If the result from a given run is not within said range, the data from said run should be discarded and the test repeated. The average of at least 3 satisfactory runs is reported.

(d) Exemplary Results

A given test solution $TS_n$ meeting the above PRM detection condition or alternative condition(s) is prepared. A second test solution $TS_c$ is prepared containing all the components of $TS_n$ at the same concentrations as in $TS_n$ except that the polymeric particles are not included. Identical procedure is carried out using a solution ($TS_c$) containing no polymeric particles (PPs). The solution $TS_c$ serves as the control solution in the test. Data are gathered at identical test conditions for a given set of test solution ($TS_c$ and $TS_n$) as described above and analyzed via headspace gas chromatography (HSGC) to determine the amount of each PRM in the headspace at each of the following three designated times: 2, 6 and 24 hours. The following tables demonstrate the type of results that can be obtained from a Longevity Test at the time point of 24 hours:

| PRM$^1$ | | PRM$^2$ | | PRM$^3$ | |
|---|---|---|---|---|---|
| $TS_c$ | $TS_n$ | $TS_c$ | $TS_n$ | $TS_c$ | $TS_n$ |
| HSGC Area Count for PRM having Low KI* (LKI) value with and without PP$^1$ | | | | | |
| 38,000 | 418,000 | 250,000 | 250,000 | 55,000 | 275,000 |
| RF = 11× | | RF = 1.0× | | RF = 4.1× | |
| ARF$_{LKI}$ = Average Response Factor ($TS_n/TS_c$) = 5.4 | | | | | |

| PRM$^4$ | | PRM$^5$ | | PRM$^6$ | |
|---|---|---|---|---|---|
| $TS_c$ | $TS_n$ | $TS_c$ | $TS_n$ | $TS_c$ | $TS_n$ |
| HSGC Area Count for PRM having High KI* (HKI) value with and without PP$^1$ | | | | | |
| 110,000 | 143,000 | 10,000 | 12,000 | 550,000 | 550,000 |
| RF = 1.3× | | RF = 1.2× | | RF = 1.0× | |
| ARF$_{HKI}$ = Average Response Factor ($TS_n/TS_c$) = 1.2 | | | | | | wherein the Response Factor (RF) is the ratio of the amount of benefit agent (e.g., perfume raw material) in the headspace collected from a substrate treated with $TS_n$ sample at a specific time point compared to the amount of the same benefit agent in the headspace collected from a substrate treated with $TS_c$ at the same time point; and the Average Response Factor (ARF) is the mean of the RFs from all measured PRMs in the test solution.

A Longevity Benefit of a perfume polymeric particle is confirmed for a particular PRM when, at any one of the three designated times points, the RF of the particular PRM is at least about 1.5, preferably at least about 3, more preferably at least about 5, and most preferably at least about 10. If the longevity benefit is confirmed, then the perfume polymeric particle falls within the scope of the present invention.

For example, the data in the above tables confirm a longevity benefit for PRM[1] and PRM[3] in the presence of PP[1], because at air drying time equals to 24 hours, both PRM/PP exhibit a greater (at least about 1.5 times) HSGC area count from $TS_n$ than that of $TS_c$.

Additionally, a perfume polymeric particle falls within the scope of the present invention if the longevity benefit is confirmed for the PRM mixture. The longevity benefit is confirmed for a PRM mixture when, at any one of the three designated time points, the RFs or ARF meet one or more of the following requirements:

1. When the Response Factor for one or more LKI perfume raw material is greater than the Response Factor for any HKI perfume raw material; or
2. When the Response Factor for one or more LKI perfume raw material is greater than the Average Response Factor (ARF) for HKI perfume raw materials; or
3. When the ARF for all measured LKI perfume raw material is greater than the ARF for all measured HKI perfume raw materials.

For example, the data in the above tables confirm a longevity benefit for perfume polymeric particles of a perfume accord containing PRM[1-6] and PP[1].

Protocol IB (Perfume Raw Material Accord Delivery or Longevity Test): Each benefit agent delivery system comprising a polymeric particle is tested in accordance with Protocol IB, in which an accord, made of selected perfume raw materials, is tested with each polymeric particle (PP) to determine if the combination of PRMs and PP(s) demonstrates an enhancement or increase in the level of PRM(s) delivered to or released from a substrate, or a sustained release time, compared to that obtained for the PRM alone.

Under Protocol IB, total of 20 PRMs (including 10 PRMs having a Kovats Index value between 1000 and 1400 and 10 PRMs having a Kovats Index value greater than 1700, all of which are selected from the representative PRMs table herein above) must be evaluated in the perfume polymeric particles as described in the above Longevity Test for test solutions ($TS_n$ and $TS_c$) with the following changes.

The relative concentration of each PRM in the mixture of 20 PRMs to be used in the Longevity Test is the concentration at which at least 18 of the 20 PRMs in the test solution is detected by HSGC in at least one of the designated time points (2, 6 or 24 hours). Note when a PRM has an HSGC area count below the instrument detection limit, it exhibits a zero value in the HSGC analysis, which such PRM shall be referred to as a "non-detected" PRM.

(a) If this detection condition is not met by $TS_0$, the overall concentration of the PRMs in the test solution is doubled and the new solution ($TS_1$) is tested in the same manner. The process is repeated until the test solutions solutions ($TS_n$ and $TS_c$) meets the detection condition set forth above, provided that the overall concentration of the PRMs in either test solution does not exceed 5 wt %.

(b) If after the concentration adjustment (up to the 5 wt % limit), the detection condition set forth above is still not met, that is, less than 18 of the 20 PRMs in the test solution are detected by HSGC at the designated time points, the relative concentrations of the 20 PRMs should be adjusted by increasing the concentrations of those non-detected PRMs in the test solution.

(c) If increasing the concentration of a specific PRM failed to meet the detection condition set forth above, the non-detected PRM(s) will be handled according to the following:

(i) if the non-detected PRM(s) is a high KI PRM, it should be replaced by an alternative high KI PRM selected from the representative table herein above; this is because the polymeric particles of the present invention are made to have affinity for low KI RPMs, thus, the response from the a high KI PRM is merely a control showing the level of delivery achieved by the polymeric particle towards a PRM having low or no affinity with the polymeric particle; and (ii) since the polymeric particles of the present invention should desirably have enhanced affinity for low KI PRMs (i.e., top notes), it can be expected that a low KI PRM may be non-detectable in $TS_c$ and becomes detectable in $TS_n$, which indicates that an enhanced delivery of said PRM to the substrate is achieved when the polymeric particle is present; in this situation, the low KI PRM of interest should not be replaced, instead, the Response Factor value for such PRM shall be defined as 10×.

(d) In addition, if any of the 20 PRMs exhibits an HSGC area count in $TS_n$ (the sample solution) that is less than the HSGC area count in $TS_c$ (the control solution), the Response Factor value for such PRM(s) shall be defined as 1.0×.

The following table demonstrates the type of results that can be obtained from a Longevity Test at the time point of 24 hours:

| HSGC Area Count for PRM having Low KI value with and without PP[1] | | | | | |
|---|---|---|---|---|---|
| PRM[1] | | PRM[2] | | PRM[3] | |
| $TS_c$ | $TS_n$ | $TS_c$ | $TS_n$ | $TS_c$ | $TS_n$ |
| ND | 418,000 | 250,000 | 250,000 | 55,000 | 275,000 |
| RF = $TS_n/TS_c$ = 10× | | RF = $TS_n/TS_c$ = 1.0× | | RF = $TS_n/TS_c$ = 4.1× | |
| $ARF_{LKI}$ = Average Response Factor ($TS_n/TS_c$) = 5.0 | | | | | |

ND = Not detected.

Polymeric particles fall within the scope of the present invention when the ARF reported for 10 of the Low Kovats Index (LKI) PRMs is greater than the ARF reported for 10 of the High Kovats Index (HKI) PRMs. Specifically, the ratio of $ARF_{LKI}/ARF_{HKI}$ is at least about 1.2, preferably at least about 2, and more preferably at least about 4. Moreover, this ratio also demonstrates a selectivity or affinity of the polymeric particles for low KI PRMs than high KI PRMs.

Protocol II (Perfume Deposition)—Fabrics are treated under normal consumer laundry conditions using fabric softener product containing 2 wt % of the perfume polymeric particles prepared for Protocol I above. A normal consumer laundry condition includes 3.2 Kg of fabric bundle load washed in 64 liters of water (6 grains per gallon hardness) at 32° C. and rinsed in water (6 ppg hardness) at 21° C., wherein the fabric bundle load typically includes nine large cotton T-shirts (100% cotton), seven polycotton pillowcases, seven polycotton hand towels, four 100% cotton terry cloths and four 86/14 cotton/poly terry wash cloths (same as the fabric used in Protocol IA). Perfume deposition is measured via fabric extraction analysis in which 0.2 grams of fabric from the 86/14 cotton/poly terry wash cloth is placed in a glass tube and heated for 20 minutes while being purged with 50 mL/min of helium. The perfume extract is collected on a Tenax® TA 60/80 trap (available from Gerstel, Inc. of Baltimore, Md.) and subsequently analyzed via GC/MS to quantitatively determine the amount of each PRM present. The results are compared to fabrics treated with fabric softener product containing the same level of perfume, but no polymeric particles. Typical increases in the level of top note PRMs provided by the present invention range from about 3 times to about 1000 times, preferably from about 5 times to about 500 times higher than for fabric treated with softener product not containing the polymeric particles. It has also been found that for fabric softener product not containing polymeric particles, some top note PRMs on fabric are below the detection limit of the GC/MS instrument. However, the presence of polymeric particles in the fabric softener product increases the level of these top note PRMs on fabric to above the detection limit.

Protocol III Polymeric Particle Affinity Test

The polymeric particles useful in the compositions of the present invention exhibit greater affinity for a PRM, which has a Kovats Index value of from about 1000 to about 1400; and one or more of the following characteristics: a molecular weight of less than about 200; a boiling point of less than about 250° C.; a ClogP of less than about 3; than its affinity for other PRMs having none of these characteristics. The following Polymeric Particle Affinity Test Protocol III can be used to determine if a polymeric particle falls within the scope of the present invention.

The polymeric particles are thoroughly mixed (via stirring, shaking, and the like) in a liquid consumer product containing perfume (such as a liquid fabric softener). The product and polymeric particles are allowed to equilibrate (e.g., for 3-4 days), during which the polymeric particles become associated (or "loaded") with one or more of the PRMs in the perfume. Then, the product and loaded polymeric particles are separated via ultra centrifugation at 40,000 rpm for 16 hours. Subsequent to centrifugation, the contents separate into distinguishable layers, e.g. a lipid layer on top, an aqueous layer in the middle, and a particle layer on the bottom. A sample from each layer is extracted with a suitable organic solvent (e.g. acetone) and analyzed via GC/MS for perfume identification using the instrument conditions given above.

The selectivity or affinity of the polymeric particle, as shown in the GC/MS analysis results, is demonstrated when the bottom particle layer is relatively enriched in PRMs having the above description of molecular weight, boiling point, ClogP and/or Kovats Index value, compared to the concentrations of the same PRMs in either of the top or middle layer. In other words, the ARF of the low KI PRMs in the bottom particle layer is at least about 1.2×, preferably at least about 4×, higher than the ARF of the low KI PRMs in the top or middle layer.

Polymeric Particle

The polymeric particle of the present invention is polymerized from at least one cationic monomer and one or more non-cationic monomers, preferably also a cross-linking monomer. The polymerization process may be any suitable process known in the art, such as emulsion, suspension or mini-emulsion polymerization. During the polymerization, an emulsifier or stabilizer may be present to keep the polymeric particles from coagulating and/or crashing out of the aqueous solution in which the polymeric particles are being formed.

The monomers of the polymeric particle may be selected such that the resulting polymeric particle has an affinity for perfume raw materials having a molecular weight of less than about 200, a boiling point of less than about 250° C., a ClogP of less than about 3, or a Kovats Index value of less than about 1700.

In another embodiment, the monomers of the polymeric particle may be selected such that the resulting polymeric particle exhibits a greater affinity and/or improved longevity benefit for a perfume raw material having a Kovats Index of from about 800 and about 1500, preferably from about 1000 to about 1500, and more preferably from about 1000 to about 1400, as measured by Protocol I and/or Protocol II described herein The polymeric particle can be derived a mixture of monomers comprising from about 50% to about 99.9%, preferably from about 60% to about 95% by weight of non-cationic monomers; from about 0.1% to about 50%, preferably from about 1% to about 10% by weight of cationic monomers; and from about 0% to about 25%, preferably from about 1% to about 10% by weight of cross-linking monomers. The weight ratio of non-cationic monomer to cationic monomer to cross-linking monomer of the mixture ranges from about 10:0.02:0 to about 5:2.5:1.

The polymeric particles may be micro-particles or nano-particles having the polymeric particle may have an average particle size of from about 100 nm to about 50 μm, as measured by light scattering using Brookhaven Particle size analyzer or Horiba particle size analyzer. In one embodiment, the polymeric particle may have an average particle size of from about 1 μm to about 39 μm, preferably from about 3 μm to about 20 μm and more preferably from about 5 μm to about 12 μm. In another embodiment, the polymeric particle may have an average particle size of from about 100 nm to about 1 μm, preferably from about 200 nm to about 900 nm and more preferably from about 700 nm to about 900 nm.

In a representative embodiment, the polymeric particles have a glass transition temperature (Tg) from about 50° C. and 150° C., preferably from about 80° C. to about 120° C.

In one embodiment, the polymeric particle may comprise a single polymer after polymerization of the monomers. In another embodiment, the polymeric particle may comprise two or more polymers, which are produced by the reaction (e.g., grafting) between the emulsifier or stabilizer and the polymerizing monomers or resulting polymeric particle. For example, the polymeric particle may comprise a first polymer resulting from the polymerization of the monomers, and a second polymer grafted or associated with the first polymer, such as polystyrene and poly(methyl methacrylate-dimethyl amino ethyl methacrylate) copolymer.

It is desirable that the polymeric particle is stable in aqueous dispersions. It is also desirable that the polymeric particle is stable within product formulations, such as perfume compositions or fabric softener compositions that contain laundry adjuncts, fabric softeners, and the like.

Stability of the polymeric particle can be influenced by factors such as the average particle size of the resulting polymeric particle, the net charge of the resulting polymeric particle, the interactions or compatibility between the polymeric particles and other ingredients in the compositions, such as emulsifiers or stabilizers.

In one embodiment, the polymeric particle has a net cationic charge about 20 mV to about 80 mV, preferably from about 30 mV to about 50 mV and more preferably from about 35 mV to about 45 mV, as measured by a Brookhaven zeta potential analyzer.

To aid in the stabilizing the polymeric particle in aqueous dispersions and/or in product formulations, such as perfume compositions, a stabilizer, also known as a colloidal stabilizer may be added to the aqueous dispersion and/or product formulation. It is desirable that the colloidal stabilizer be compatible with other ingredients within the aqueous dispersion and/or product formulation.

The polymeric particle may be water-insoluble. In other words, when added to water, the polymeric particle physically separates from the water (i.e., settles-out, flocculates, emulsifies, or floats) within 5 minutes after addition, whereas a material that is "soluble in water" does not physically separate from the water within 5 minutes after addition. It is not required that the physical separation be visible to the naked eyes. The physical separation can be detectable by instruments, such as light scattering or refraction. Another way of describing water-insoluble materials for purposes of the present invention is the fact that water-insoluble materials are not soluble in distilled (or equivalent) water, at 25° C., at a concentration of greater than about 5%, preferably greater than about 3% and more preferably greater than about 1% by weight of the mixture containing water and polymeric particles.

The polymeric particle may have a weight-average molecular weight of from about 1,000 to about 2,000,000 preferably from about 5,000 to about 1,000,000, more preferably from about 10,000 to about 750,000, more preferably from about 20,000 to about 500,000 daltons. The weight-average molecular weight of the polymeric particle, can be determined via conventional methods such as gel permeation chromatography.

A. Non-Cationic Monomer

The non-cationic monomer may be a hydrophobic group-containing monomer. Examples of the hydrophobic group include, but are not limited to, alkyls, cycloalkyls, aryls, alkaryls, aralkyls and mixtures thereof.

The non-cationic monomer may be a hydroxyl-containing monomer, an anionic group-containing monomer, or a zwitterionic monomer. The non-cationic monomer include, but are not limited to, ethylene glycol phenyl ether acrylate (EGPhA), trans-cinnamic acid, 2-ethyl hexyl acrylate, and mixtures thereof.

Nonlimiting examples of suitable non-cationic monomers include, but are not limited to, methyl methacrylate, methyl acrylate, ethyl acrylate, n-propyl acrylate, iso-propyl acrylate, n-butyl acrylate, isobutyl acrylate, hydroxyethyl acrylate, hydroxypropyl acrylate, benzyl acrylate, ethylhexyl acrylate, n-propyl methacrylate, ethyl methacrylate, iso-propyl methacrylate, isobutyl methacrylate, n-butyl methacrylate, methacrylic acid, acrylic acid, acrylamide, methacrylamide, styrene, α-methyl styrene, hydroxyethyl methacrylate, hydroxypropyl methacrylate, hydroxybutyl acrylate, hydroxybutyl methacrylate, PEG acrylate, phenyl methacrylamide, t-butyl methacrylamide, p-hydroxyphenyl methacrylamide, vinyl ethers, vinyl ketones, vinyl acetates, vinyl phenols, acylamido-2-methylpropanesulfonic acid, vinlysulfonate, vinylpropionate, methylallylsulfonic acid, N-vinyl formamide and N-vinylpyrrolidone.

B. Cationic Monomer

The cationic monomer of the present invention comprises a cationic unit. For the purposes of the present invention the term "cationic unit" is defined as a moiety which when incorporated into the structure of the polymeric particle of the present invention, is capable of maintaining a cationic charge within the pH range of from about 2 to about 8. The cationic unit is not required to be protonated at every pH value within the range of about 2 to about 8. Non-limiting examples of units which comprise a cationic moiety include the cationic units having the formula:

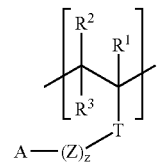

wherein each of $R^1$, $R^2$ and $R^3$ are independently selected from hydrogen or $C_1$ to $C_6$ alkyl, and preferably hydrogen, $C_1$ to $C_3$ alkyl, more preferably, hydrogen or methyl; T is a substituted or unsubstituted, saturated or unsaturated, linear or branched moiety selected from the group consisting of alkyl, cycloalkyl, aryl, alkaryl, aralkyl, heterocyclic ring, silyl, nitro, halo, cyano, sulfonato, alkoxy, keto, ester, ether, carbonyl, amido, amino, glycidyl, carbanato, carbamate, carboxylic, carboalkoxy, and mixtures thereof; Z is a moiety selected from the group consisting of: —($CH_2$)—, ($CH_2$—CH=CH)—, —($CH_2$—CHOH)—, ($CH_2$—$CHNR^4$)—, —($CH_2$—$CHR^5$—O)— and mixtures thereof, preferably —($CH_2$)—, wherein $R^4$ and $R^5$ are independently selected from hydrogen or $C_1$ to $C_6$ alkyl, preferably hydrogen, methyl, ethyl; z is an integer from 0 to 12, preferably from 2 to 10, more preferably from 2 to 6; A is $NR^6R^7$ or $NR^6R^7R^8$, wherein each of $R^6$, $R^7$ and $R^8$ are independently selected from H, $C_1$-$C_8$ linear or branched alkyl, or alkyleneoxy having the formula:

wherein $R^9$ is $C_2$ to $C_4$ linear or branched alkylene or carbonyl alkyl; $R^{10}$ is hydrogen or $C_1$ to $C_4$ alkyl,; y is from 1 to about 10. In one embodiment, $R^6$, $R^7$ and $R^8$ are independently, hydrogen, $C_1$ to $C_4$ alkyl. Alternatively, $NR^6R^7$ or $NR^6R^7R^8$ can form a heterocyclic ring containing from 4 to 7 carbon atoms, optionally containing additional hetero atoms, optionally fused to a benzene ring, and optionally substituted by $C_1$ to $C_8$ hydrocarbyl, or acetates. Examples of suitable heterocycles, both substituted and unsubstituted, are indolyl, isoindolinyl imidazolyl, imidazolinyl, piperidinyl pyrazolyl, pyrazolinyl, pyridinyl, piperazinyl, pyrrolidinyl, pyrrolidinyl, guanidino, amidino, quinidinyl, thiazolinyl, morpholine and mixtures thereof, with morpholino and piperazinyl being preferred.

Nonlimiting examples of suitable cationic monomers for the present invention include, but are not limited to, dimethylamino alkyl acrylates, especially dimethylaminoethyl methacrylate, vinyl pyrrolidones, vinyl imidazoyls, vinyl ethers having dialkyl amino groups, vinyl pyridines, alkyl acrylamides, dialkylamino alkyl acrylamides, and amino alkyl acrylamides.

C. Cross-linking Monomer

The cross-linking monomer may be present in the polymeric particle of the present invention. Nonlimiting examples of suitable cross-linking monomers include, but are not limited to, diacrylate, dimethacrylate, diethylene glycol diacrylate, divinylbenzene, divinyl ether, ethylene glycol dimethacrylate, pentaerythritol triacrylate, polyallyl sucrose, trivinyl benzene, divinyl toluene, trivinyl toluene, triethylenglycol dimethacrylate, tetraethylenglycol dimethacrylate, allylmethacrylate, diallylmaleate, triallylmaleate and 1,4-butanediol diacrylate, triallylmaleate 1,2-ethanediol diacrylate, 1,3-propanediol diacrylate, 1,6-hexanediol diacrylate, divinyl bezene, and ethylene glycol diacylate.

D. Emulsifier or Colloidal Stabilizer

Suitable emulsifiers and/or colloidal stabilizers for use in the present invention are known in the art. Nonlimiting examples of such emulsifiers or colloidal stablizers include, but are not limited to, ricinolyamidopropyltrimethyl-ammoniummetho sulfate, cocopentylethoxymethyl-ammoniummethyl sulfate, cocobis(2-hydroxyethyl) methylammonium chloride, cetyltrimethylammonium bromide, cetylpyridinium chloride, glyceryl stearate, stearadamidoethyl diethylamine, ethoxylated oleylamines, ethoxylated fatty amines, ethoxylated quaternised fatty amines, ethoxylated fatty alcohols, sorbitan stearate, polysorbate, stearate, sodium dodecyl sulfate, ammoniumnonoxynol sulfate, dodecyltrimethyl ammonium bromide, sodium lauryl sulfate, sodium laurate, gelatine, polyvinylalcohol, aminomethylated starch, poly(vinylalcohol-co-vinylacetate) copolymers, modified cellulose cellulose like carboxymethyl cellulose, methyl cellulose, hydroxyethyl cellulose, polyoxyethylene, polyvinylpyrrolidone, polyoxyethylene-polyoxypropylene-polyoxyethylene copolymers, polyether-modified dimethicones and polyether-alkyl-dimethicones copolymers, cationic silicones and polyimides.

A colloidal stabilizer may be used to maintain particle dispersive stability, particularly of larger sized particles. Suitable colloidal stabilizer include, but are not limited to, propylene oxide-ethylene oxide copolymers or ethyleneoxide-propylenoxide graphted polyethylenimines, polyoxyethylene (X) isooctylphenyl ether where X is an integer from 20 to 80, fatty alcohol ethoxylates, polyethoxylated polyterephthalate block co-polymers polyvinylpyrrolidone polyvinylpyrrolidone and copolymers containing vinylpyrolidone.

E. Initiators

Suitable initiators for use in the polymerization process of the present invention are known in the art. Examples include, but are not limited to sodium persulfate and azo initiators, such as 2,2'-azobis(2-methylpropionamide)dihydrochloride; 2,2'-azobis(2-amidinopropane)dihydrochloride; 2,2'-azobis(N,N'-dimethyleneisobutyramidine)dihydrochloride; 2,2'-azobis(2-methylbutyronitrile); 2,2'-azobis (4-methoxy-2,4-dimethylvaleronitrile); and 2-(Carbamoylazo)-isobutyronitrile.

Synthesis Examples for Preparing Polymeric Particle

EXAMPLE 1

Microparticles

| | |
|---|---|
| 1080 g | of water |
| 160 g | of a 10% solution of a 88% hydrolysed poly vinyl acetate (wherein the viscosity of a 4% aqueous solution is 40 mPas), alternatively referred to as "poly vinyl alcohol" |
| 510 g | of methyl methacrylate |
| 60 g | of butanediol diacrylate |
| 30 g | of dimethylaminoethyl methacrylate |
| 3.8 g | of t-butyl perpivalate |
| Feedstream 1: 1.08 g of t-butyl hydroperoxide, 70% strength in water | |
| Feedstream 2: 0.38 g of ascorbic acid, 14 g of water | |

The above substances are initially introduced at room temperature with exception of the perpivalate, and are adjusted to a pH of 6 with 10% strength hydrochloric acid. The water and monomer phase are dispersed using a high-speed dissolver stirrer at 2500 rm. After 40 minutes of dispersing, a stable emulsion with an average particle size of from 2 to 12 microns (diameter) is obtained. The t-butyl perpivalate is added and the emulsion is first heated to 72° C., while stirring with an anchor stirrer, then heated to 85° C. over the course of a further 120 minutes, and holding at 85° C. over the course of a further 60 minutes. The resulting microparticle dispersion is cooled with stirring to 70° C., and feedstream 1 is added. Feedstream 2 is metered in with stirring over 80 minutes at 70° C. The composition is then cooled, and the resulting microparticle dispersion has a solids content of 31.2% and a particle size comparable to the average particle size of the emulsion prior to polymerization.

EXAMPLE 2

Microparticles

Example 1 is repeated as described with the following monomer mixture: 390 g of methyl methacrylate, 180 g of styrene and 30 g of dimethylaminoethyl methacrylate. The resulting microparticle dispersion has a solids content of 31.1% and a volume median particle size 9.6 µm.

EXAMPLE 3

Nanolatex Particles

Distilled and deionized water (943.85 g) and 37% hydrochloric acid (4.95 g) are placed into a 2000 ml three-necked round-bottomed flask, fitted with a heating mantle, an anchor type mechanical stirrer, an internal thermometer, a reflux condenser and an argon gas inlet. 2-(dimethylamino) ethyl methacrylate (5.26 g) is added with stirring. Methyl methacrylate (100.00 g), cetyl pyridinium chloride (6.0 g) and 2,2'-azobis(2-methylpropionamide) dihydrochloride (1.06 g) are added with stirring. Heat is applied with stirring and a temperature of 75° C. is reached after 1 hour. The mixture is stirred for 16 hours at 70° C. and filtered through an ASTM 4-8 µm glass-fritted funnel. Reduced pressure rotary evaporation is used to concentrate the product to a nanolatex emulsion having about 30% polymer content and an average particle size of 170 nm (diameter).

EXAMPLE 4

Nanolatex Particles

In a 2 liter flask fitted with a heating mantle, an anchor type mechanical stirrer, an internal thermometer, a reflux condenser and an argon gas inlet is placed 17 g methyl methacrylate, 0.4 g sulphuric acid (50%), 4.5 g styrene, 1.2 g dimethylaminoethyl methacrylate, 3.4 g oleylaminoethoxylatequat (Lipamin OK, 40% aqueous solution), 7.9 g of 2,2'-azobis(2-amidineopropane)dihydrochloride (V-50, 2.5% aqueous solution), and 566 g water. Heat is applied with stirring and a temperature of 85° C. is reached after 10 minutes. Continuous addition in 180 min at a stir rate of 130 rpm of 320.5 g methyl methacrylate, 8.6 g sulphuric acid, 85.5 g styrene, 64 g oleylaminoethoxylatequat, 68.9 g 2,2'-azobis(2-amidineopropane)dihydrochloride (2.5% aqueous solution), and 396.7 g deionised water is performed. The mixture is stirred for 0.5 hours at 85° C. An aqueous dispersion (30% solids content) with a pH of 5.2 and average particle size of about 150 nm (diameter) is obtained.

EXAMPLE 5

Nanolatex Particles

In a 2 liter flask fitted with a heating mantle, an anchor type mechanical stirrer, an internal thermometer, a reflux condenser and an argon gas inlet is placed 1.5 g sulfuric acid (50%), 20.0 g polyvinylalcohol (88% hydrolyzed), 4.0 g of 2,2'-azobis(2-amidineopropane)dihydrochloride (V-50, 2.5% aqueous solution), and 953 g water. Heat is applied with stirring and a temperature of 85° C. is reached after 10 minutes. Continuous addition in 105 min at a stir rate of 150 rpm of 95 g methyl methacrylate, 6.25 g dimethylaminoethylacrylatemethochloride, and 116 g 2,2'-azobis(2-amidineopropane)dihydrochloride (2.5% aqueous solution) produces an aqueous dispersion (10% solids content) with a pH of 2 and average particle size of 110 nm (diameter).

EXAMPLE 6

Nanolatex Particles

In a 2 liter flask fitted with a heating mantle, an anchor type mechanical stirrer, an internal thermometer, a reflux condenser and an argon gas inlet is placed 0.3 g allyl methacrylate, 17.5 g methyl methacrylate, 0.3 g sulfuric acid (50%), 0.9 g dimethylaminoethyl methacrylate, 2.8 g oleylaminoethoxylatequat (Lipamin OK, 40% aqueous solution), 6.3 g of 2,2'-azobis(2-amidineopropane)dihydrochloride (V-50, 2.5% aqueous solution), and 463 g water. Heat is applied with stirring and a temperature of 80° C. is reached after 10 minutes. Continuous addition in 210 min at a stir rate of 180 rpm of 3.4 g allyl methacrylate, 334 g methyl methacrylate, 6.1 g sulphuric acid, 52.5 g oleylaminoethoxylatequat, 56.7 g 2,2'-azobis(2-amidineopropane) dihydrochloride (2.5% aqeous solution), and 326.5 g deionised water is performed. The mixture is stirred for 0.5 hours at 80° C. An aqueous dispersion (30% solids content) with a pH of 5.6 and average particle size of about 180 nm (diameter) is obtained.

EXAMPLE 7

Core/Shell-Nanolatex Particles

In a 2 liter flask fitted with a heating mantle, an anchor type mechanical stirrer, an internal thermometer, a reflux condenser and an argon gas inlet is placed 7.4 g methyl methacrylate, 0.2 g sulphuric acid (50%) 2.3 g Triton X405 (70% aqueous solution), 6.3 g of 2,2'-azobis(2-amidineopropane)dihydrochloride (V-50, 2.5% aqueous solution), and 455 g water. Heat is applied with stirring and a temperature of 90° C. is reached after 10 minutes. Continuous addition in 90 min at a stir rate of 140 rpm of 5.4 g Triton® X-405, 140.6 g methyl methacrylate, 4.2 g sulfuric acid, 25.0 g 2,2'-azobis(2-amidineopropane)dihydrochloride (2.5% aqueous solution), and 130.0 g deionised water is performed. The mixture is stirred for 0.5 hours at 80° C. Continuous addition in 120 min at a stir rate of 140 rpm of 33.3 g oleylaminoethoxylatequat (Lipamin OK, 40% aqueous solution), 166.5 g methyl methacrylate, 3.0 g sulphuric acid, 31.8 g 2,2'-azobis(2-amidineopropane)dihydrochloride (2.5% aqueous solution), and 206 g deionised water is performed. The mixture is stirred for 0.5 hours at 85° C. An aqueous dispersion (29.3% solids content) with a pH of 2.3 and average particle size of from about 100 nm (diameter) is obtained.

EXAMPLE 8

Nanolatex Particles

In a 2 liter flask fitted with a heating mantle, an anchor type mechanical stirrer, an internal thermometer, a reflux condenser and an argon gas inlet is placed 9.1 g 2-ethylhexyl acrylate, 10.2 g methyl methacrylate, 0.35 g sulfuric acid (50%), 1.0 g dimethylaminoethyl methacrylate, 3.8 g cetylpyridinium chloride, 6.3 g of 2,2'-azobis(2-amidineopropane)dihydrochloride (V-50, 2.5% aqueous solution), and 464 g water. Heat is applied with stirring and a temperature of 80° C. is reached after 10 minutes. Continuous addition in 210 min at a stir rate of 130 rpm of 174 g 2-ethylhexyl acrylate, 193.3 g methyl methacrylate, 6.1 g sulphuric acid, 3.8 g cetyl pyridinium chloride, 63.0 g 2,2'-azobis(2-amidineopropane)dihydrochloride (2.5% aqueous solution), and 360 g deionised water is performed. The mixture is stirred for 0.5 hours at 80° C. An aqueous dispersion 30% solids content of a pH of 6.6 and average particle size of about 170 nm (diameter) is obtained.

EXAMPLE 9

Nanolatex Particles

In a 2 liter flask fitted with a heating mantle, an anchor type mechanical stirrer, an internal thermometer, a reflux condenser and an argon gas inlet is placed 7.0 g acrylic acid, 20.0 g dimethylaminoethyl methacrylate, 253.9 g deionized water, 15.75 g sulfuric acid (50%), and 15.7 g sodium peroxodisulfate (7% aqueous solution). Heat is applied with stirring and a temperature of 95° C. is reached after 15 minutes and maintained for another 60 minutes. Deionized water (560 g) is added and the temperature maintained at 85° C. for 30 minutes. Continuous addition in 120 min at a stir rate of 150 rpm of 190 g methyl methacrylate, and 25.1 g sodium peroxodisulfate (7% aqueous solution) gave an aqueous dispersion 19.7% solids content of a pH of 2.1 and average particle size of about 250 nm (diameter) is obtained.

EXAMPLE 10

Nanolatex Particles

In a 2 liter flask fitted with a heating mantle, an anchor type mechanical stirrer, an internal thermometer, a reflux condenser and an argon gas inlet is placed 7.0 g acrylic acid, 20.0 g dimethylaminoethyl methacrylate, 253.9 g deionized water, 15.75 g sulfuric acid (50%), and 15.7 g sodium peroxodisulfate (7% aqueous solution). Heat is applied with stirring and a temperature of 95° C. is reached after 15 minutes and maintained for another 60 minutes. Deionized water (560 g) is added and the temperature is maintained at 85° C. for 30 minutes. Continuous addition in 120 min at a stir rate of 150 rpm of 190 g methyl methacrylate, and 25.1 g sodium peroxodisulfate (7% aqueous solution) produces an aqueous dispersion of 19.7% solids content of a pH of 2.1 and average particle size of about 250 nm (diameter) is obtained.

EXAMPLE 11

Nanolatex Particles

In a 2 liter flask fitted with a heating mantle, a heating mantle, an anchor type mechanical stirrer, an internal thermometer, a reflux condenser and an argon gas inlet is placed 0.9 g sodium hydroxide (10% aqueous solution), 20.0 g polyvinylalcohol (88% hydrolyzed), and 954 g water. Heat is applied with stirring and a temp of 85° C. is reached after 10 minutes. Temperature is adjusted to 75° C. and 4.0 g of 2,2'-azobis(2-amidineopropane)dihydrochloride (2.5% aqueous solution) is added. Continuous addition in 105 min at a stir rate of 150 rpm of 95 g methyl methacrylate, 5.0 g dimethylaminopropyl methacrylamide, and 116 g 2,2'-azobis(2-amidineopropane)dihydrochloride (2.5% aqueous solution) produces an aqueous dispersion (10% solids content) with a pH of 6.8 and average particle size of 133 nm (diameter).

Perfume Polymeric Particle

In one embodiment, the perfume polymeric particle comprises a perfume, which comprises greater than 50%, by weight of the perfume, of perfume raw materials having a molecular weight of less than about 200, a boiling point of less than about 250° C. and a ClogP of less than about 3 and/or a Kovats Index value of less than about 1700. In another embodiment, the perfume comprises at least 10%, preferably at least 20%, and more preferably at least 30%, by weight of the perfume, of low KI perfume raw material.

In still another embodiment, the perfume polymeric particle is loaded with perfume such that from about 1 to about 90 wt %, preferably from about 5 to about 60 wt % of the added perfume is loaded into the polymeric particle.

Composition

The perfume polymeric particle of the present invention may be incorporated along with one or more adjunct ingredients to form a perfume-containing composition, referred to as the perfume composition. Examples of compositions suitable for incorporating perfume polymeric particles therein are disclosed in U.S. Pat. No. 4,994,193 and U.S. Pat. No. 5,767,052.

The perfume polymeric particle may be present in the perfume composition at any suitable level, typically it is present at a level of from about 0.1% to about 20%, preferably from about 1% to about 10%, and more preferably from about 1% to about 5% by weight of the perfume composition.

The perfume composition of the present invention may be in any suitable form, such as liquids, gels, foams, paste, granules, and tablets.

Adjunct Ingredients

Nonlimiting examples of suitable adjunct ingredients for inclusion in the perfume compositions of the present invention include, but are not limited to, surfactants, fabric softening agents, suds boosting agents, suds suppressors, perfume, soil release agents, fatty acids, dyes, colorants, antibacterial agents and electrolytes.

When the adjunct ingredient is a fabric softening agent (also referred to as "softening active"), the perfume composition is referred to as a fabric softener composition. The fabric softener composition can include a liquid fabric softener composition and a rinse-added liquid fabric softener composition. In one embodiment, the weight ratio of perfume polymeric particle to fabric softening agent is from about 1:10 to about 1:0.5, preferably from about 1:5 to about 1:1. In another embodiment, the weight ratio of perfume polymeric particle to adjunct ingredient is from about 20:1 to about 1:20, preferably from about 5:1 to about 1:5.

Nonlimiting examples of suitable fabric softening agents include, but are not limited to: diester quaternary ammonium fabric softening active compounds (DEQA) and polyquaternary ammonium compounds.

(1) The first type of DEQA preferably comprises, as the principal active, compounds of the formula:

wherein each R substituent is selected from hydrogen; a short chain $C_1$-$C_6$ alkyl or hydroxyalkyl, preferably methyl, ethyl, propyl, or hydroxyethyl, and more preferably methyl; poly($C_1$-$C_3$ alkoxy), preferably polyethoxy; benzyl; or a mixture thereof; each m is 2 or 3; each n is from 1 to about 4; each Y is —O—(O)C—, —C(O)—O—, —NR—C(O)—, or —C(O)—NR—; the sum of carbons in each $R^1$, plus one when Y is —O—(O)C— or —NR—C(O)—, is $C_{12}$-$C_{22}$, preferably $C_{14}$-$C_{20}$, with each $R^1$ being a hydrocarbyl, or substituted hydrocarbyl group, and $A^-$ can be any softener-compatible anion, preferably, chloride, bromide, methylsulfate, ethylsulfate, sulfate, and nitrate, more preferably chloride or methyl sulfate. (As used herein, the "percent of softening active" containing a given $R^1$ group is based upon taking a percentage of the total active based upon the percentage that the given $R^1$ group is, of the total $R^1$ groups present.).

(2) A second type of DEQA active has the general formula:

wherein each Y, R, $R^1$, and $A^-$ have the same meanings as before. Such compounds include those having the formula:

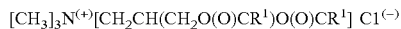

where each R is a methyl or ethyl group and preferably each $R^1$ is in the range of $C_{15}$ to $C_{19}$.

(3) The DEQA actives described hereinabove also include the neutralized amine softening actives wherein at least one R group is a hydrogen atom. A non-limiting example of actives of this type is the chloride salt of (unsaturated alkoyloxyethyl)(unsaturated alkylamidotrimethylene)methylamine. Other examples of suitable amine softening actives are disclosed in PCT application WO 99/06509.

(4) Polyquaternary Ammonium Softening Actives. Fabric softening actives carrying more than one positive quaternary ammonium charge are also useful in the rinse-added compositions of the present invention. An example of this type of softening active is that having the formula:

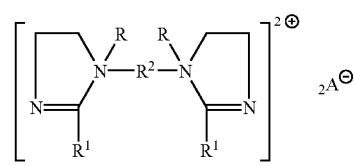

wherein each R is H, a short chain $C_1$-$C_6$ alkyl or hydroxyalkyl, preferably methyl, ethyl, propyl, or hydroxyethyl, and the like, more preferably methyl, benzyl, or $(R^2O)_{2-4}H$; each $R^1$ is a $C_6$-$C_{22}$, preferably $C_{14}$-$C_{20}$ hydrocarbyl, or substituted hydrocarbyl substituent, preferably $C_{10}$-$C_{20}$ alkyl or alkenyl (unsaturated alkyl, including polyunsaturated alkyl, also referred to sometimes as "alkylene"), most preferably $C_{12}$-$C_{18}$ alkyl or alkenyl; each $R^2$ is a $C_1$-$C_6$ alkylene group, preferably an ethylene group; and $A^-$ are defined as below.

(5) Softening active having the formula:

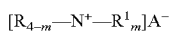

wherein each m is 2 or 3, each $R^1$ is a linear or branched, saturated or unsaturated $C_6$-$C_{22}$ moiety, preferably $C_{14}$-$C_{20}$ moiety, but no more than one being less than about $C_{12}$ and then the other is at least about $C_{16}$; or hydrocarbyl or substituted hydrocarbyl substituent, preferably $C_{10}$-$C_{20}$ alkyl or alkenyl, most preferably $C_{12}$-$C_{18}$ alkyl or alkenyl.

Examples of Compound (5) are dialkylenedimethylammonium salts, such as commercially available dialkylenedimethylammonium salts usable in the present invention is dioleyldimethylammonium chloride available from Witco Corporation under the trade name Adogen® 472.

Other examples of Compound (5) are the monoalkenyltrimethylammonium salts such as monooleyltrimethylammonium chloride, monocanolatrimethylammonium chloride, and soyatrimethylammonium chloride. Monooleyltrimethylammonium chloride and monocanolatrimethylammonium chloride are preferred.

(6) Softening active having the formula:

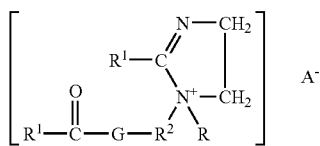

wherein each R, $R^1$, and $A^-$ have the definitions given above; each $R^2$ is a $C_1$-$C_6$ alkylene group, preferably an ethylene group; and G is an oxygen atom or an —NR— group.

An example of Compound (6) is 1-methyl-1-oleylamidoethyl-2-oleylimidazolinium methylsulfate, which is available commercially from the Witco Corporation under the trade name Varisoft® 3690.

Other examples of Compound (6) are substituted imidazolinium salts having the formula:

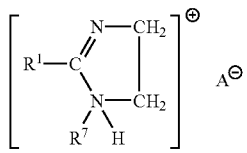

wherein $R^7$ is hydrogen or a $C_1$-$C_4$ saturated alkyl or hydroxyalkyl group, and $R^1$ and $A^-$ are defined as hereinabove.

(7) Softening active having the formula:

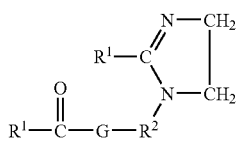

wherein $R^1$, $R^2$ and G are defined as above in (6).

(8) Reaction products of substantially unsaturated and/or branched chain higher fatty acids with dialkylenetriamines in, e.g., a molecular ratio of about 2:1, said reaction products containing compounds of the formula:

wherein $R^1$, $R^2$ are defined as above in (6), and each $R^3$ is a $C_1$-$C_6$ alkylene group, preferably an ethylene group. Examples of Compound (8) include Emersol® 223LL and Emersol® 7021, which are available from Henkel Corporation.

(9) Softening active having the formula:

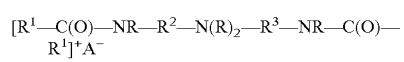

wherein R, $R^1$, $R^2$, $R^3$ and $A^-$ are defined as above in (6) and (8). An example of Compound (9) is a difatty amidoamine based softening active available commercially from the Witco Corporation under the trade name Varisoft® 222LT.

(10) The reaction product of substantially unsaturated and/or branched chain higher fatty acid with hydroxyalkylalkylenediamines in a molecular ratio of about 2:1, said reaction products containing compounds of the formula:

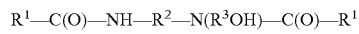

wherein $R^1$, $R^2$ and $R^3$ are defined as above in (8). Examples of Compound (10) include reaction products of oleic acids with N-2-hydroxyethylethylenediamine in a molecular ratio of about 2:1, said reaction product mixture containing a compound of the formula:

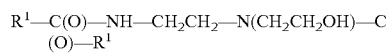

wherein $R^1$—C(O) is oleoyl group of a commercially available oleic acid derived from a vegetable or animal source, such as Emersol® 223LL or Emersol® 7021, available from Henkel Corporation.

(11) Alkylpyridinium salts having the formula:

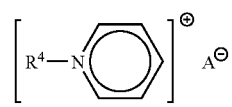

wherein $R^4$ is an acyclic aliphatic $C_8$-$C_{22}$ hydrocarbon group and $A^-$ is an anion.

(12) Alkanamide alkylene pyridinium salts having the formula:

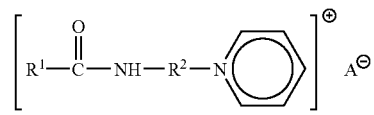

wherein $R^1$, $R^2$ and $A^-$ are defined as herein above;

(13) Monoalkyl diquaternary salts, e.g., that having the formula:

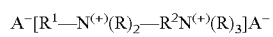

wherein R, $R^1$, $R^2$ and $A^-$ are defined as herein above in (6) and (9).

An example of Compound (13) is N-tallow pentamethyl propane diammonium dichloride, with the formula:

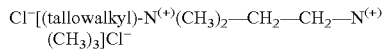

available from Witco Corporation under the trade name Adogen® 477.

(14) Mixtures of compounds (1)-(13) disclosed above.

In the cationic nitrogenous salts herein, the anion $A^-$, which is any softening active compatible anion, provides electrical neutrality. Most often, the anion used to provide electrical neutrality in these salts is from a strong acid, especially a halide, such as chloride, methylsulfate, bromide, or iodide. However, other anions can be used, such as ethylsulfate, acetate, formate, sulfate, carbonate, and the like. Chloride and methylsulfate are preferred herein as anion A.

Preparation of Benefit Agent Delivery System And Product

The benefit agent delivery system comprising the polymeric particles and the benefit agents can be prepared in two ways. One is the separate addition mode wherein the polymeric particle and the benefit agent are separately added to a product matrix (a liquid or a granule) in a manner similar to adding an ingredient to the product matrix in preparing the final product formulation. In the separate addition mode, the formation of the benefit agent delivery system is facilitated by the polymeric particle's affinity for the benefit agent it is designed for. Thorough mixing is frequently carried out using high shear agitation. A gentle heating to about 40° C. to about 65° C. may be used. Essential or adjunct ingredients may also be added to the matrix in order to form the complete end product into which the delivery system is to be incorporated.

The alternative way to prepare the benefit agent delivery system is the pre-loading method wherein the polymeric particles and the benefit agents are mixed directly to prepare the benefit agent delivery system, e.g., a perfume polymeric particle. This pre-loading step is typically done in the presence of a solvent, such as water or lower alcohols, to facilitate the mixing process. In a typical embodiment, the solvent used during the synthesis of the polymeric particle is sufficient. The pre-loaded benefit agent delivery system can then be added to a product matrix (a liquid or a granule) in a manner similar to adding an essential or adjunct ingredient to prepare the final product. High shear agitation and gentle heating can be used in the pre-loading step or the subsequent product formulating step.

In a typical embodiment, the polymeric particles, typically in the form of an aqueous dispersion (about 30 wt % polymer in water), and the perfume (a mixture of PRMs are pre-mixed in a higher shear mixer at room temperature. Additional solvent (such as water or lower alcohols) may be used, though it is not required. The pre-mixing time ranges from about 15 minutes to about 16 hours. It is found that after about 4 hours, approximately 90 wt % of the added perfume are loaded onto the polymeric particle. The pre-loaded perfume polymeric particles can be added to a product matrix and allowed to equilibrate for at least about 1 week, preferably at least about 2 weeks, before the product is put to use.

FORMULATION EXAMPLES

The following are examples of perfume compositions, especially fabric softener compositions according to the present invention.

| Component | A | B | C | D |
|---|---|---|---|---|
| DEQA | 19.0 | 18.0 | 25.0 | 20.0 |
| Fatty acid | — | 1.0 | — | 1.0 |
| Hydrochloric acid | 0.02 | 0.02 | 0.02 | 0.2 |
| Soil Release Polymer | 0.02 | 0.02 | 0.02 | 0.2 |
| PEG | 0.6 | 0.6 | — | 0.6 |
| Perfume | 1.0 | 1.0 | 1.0 | 1.0 |
| Polymeric Particles | 2.0 | 5.0 | 0.5 | 1.0 |
| Eletrolyte | 600 ppm | 600 ppm | 600 ppm | 600 ppm |
| Dye | 50 ppm | 50 ppm | 50 ppm | 50 ppm |
| Water | Balance | Balance | Balance | Balance |

| Component | E | F | G | H |
|---|---|---|---|---|
| DEQA | 19.0 | 18.0 | 25.0 | 20.0 |
| Fatty acid | — | 1.0 | — | 1.0 |
| Hydrochloric acid | 0.02 | 0.02 | 0.02 | 0.2 |
| Soil Release Polymer | 0.02 | 0.02 | 0.02 | 0.2 |
| PEG | 0.6 | 0.6 | — | 0.6 |
| Perfume Polymeric Particles | 2.0 | 5.0 | 0.5 | 1.0 |
| Eletrolyte | 600 ppm | 600 ppm | 600 ppm | 600 ppm |
| Dye | 50 ppm | 50 ppm | 50 ppm | 50 ppm |
| Water | Balance | Balance | Balance | Balance |

In examples A-D, the polymeric particles are added separately to the fabric softener composition. In examples E-H, the polymeric particles and perfume are pre-mixed together prior to addition to the fabric softener composition.

All documents cited, including the priority document, are, in relevant part, incorporated herein by reference; the citation of any document is not to be construed as an admission that it is prior art with respect to the present invention.

While particular embodiments of the present invention have been illustrated and described, it would be apparent to those skilled in the art that various other changes and modifications can be made without departing from the spirit and scope of the invention. It is therefore intended to cover in the appended claims all such changes and modifications that are within the scope of this invention.

What is claimed is:

1. A method for making an aqueous fabric softening compostion having pH from about 2 to about 8 with improved delivery of perfume raw material, said method comprising preparing a perfume polymeric particle by mixing:

a) a polymeric particle comprising a monomer which is in its protonated cationic form in aqueous media at a pH within the range of about 2 to about 8 having the formula:

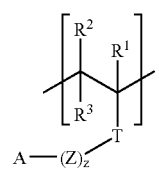

[I]

wherein each of $R^1$, $R^2$ and $R^3$ are independently selected from hydrogen or $C_1$ to $C_6$ alkyl; T is a carboxylic moiety; Z is $—(CH_2)—$; z is 2; A is $NR^6R^7$ wherein $R^6$ and $R^7$ are independently selected from H, $C_1$-$C_8$ linear or branched alkyl, or alkyleneoxy having the formula:

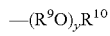

wherein $R^9$ is $C_2$-$C_4$ linear or branched alkylene, carbonyl alkyl, or mixtures thereof; $R^{10}$ is hydrogen, $C_1$-$C_4$ alkyl carbonyl alkyl, or mixtures thereof; y is an integer from 1 to 10; and b) a perfume comprising a perfume raw material having a Kovats Index value of from about 1000 to about 1400 and optionally one or more of the following characteristics:

a molecular weight of less than about 200;

a boiling point of less than about 250° C.; or a ClogP of less than about 3;

wherein the polymeric particle has a net cationic charge at a pH from about 2 to about 8 from about 20 mV to about 80 mV, a particle size in the range from about 100 nanometers to about 50 micrometers and a Response Factor (RF) of the perfume polymeric material is at least about 1.5, as measured by Longevity Test Protocols I or II, said perfume being non-encapsulated by and non-polymerically associated with the polymer, and c) adding said perfume polymeric particles to a product matrix comprising a fabric softening agent.

2. The method according to claim 1 wherein the cationic monomer of said polymer is dimethylaminoethyl methacrylate.

3. The method according to claim 1 wherein the polymeric particle further comprises a non-cationic monomer.

4. The method according to claim 3 wherein the non-cationic monomer is selected from the group consisting of: methyl methacrylate, methyl acrylate, ethyl acrylate, n-propyl acrylate, iso-propyl acrylate, n-butyl acrylate, isobutyl acrylate, hydroxyethyl acrylate, hydroxypropyl acrylate, benzyl acrylate, ethylhexyl acrylate, n-propyl methacrylate, ethyl methacrylate, iso-propyl methacrylate, isobutyl methacrylate, n-butyl methacrylate, methacrylic acid, acrylic acid, acrylamide, methacrylamide, styrene, α-methyl styrene, hydroxyethyl methacrylate, hydroxypropyl methacrylate, hydroxybutyl acrylate, hydroxybutyl methacrylate, PEG acrylate, phenyl methacrylamide, t-butyl methacrylamide, p-hydroxyphenyl methacrylamide, vinyl ethers, vinyl ketones, vinyl acetates, vinyl phenols, acylamido-2-methylpropanesulfonic acid, vinlysulfonate, vinylpropionate, methylallylsulfonic acid, N-vinyl formamide and N-vinylpyrrolidone, and mixtures thereof.

5. The method according to claim 1 wherein the perfume polymeric particle has an average particle size of from about 1 μm to about 39 μm.

6. The method according to claim 1 wherein the perfume polymeric particle has an average particle size of from about 200 nm to about 900 nm.

7. The method according to claim 1 wherein the polymer is a water-insoluble polymer.

8. The method according to claim 1 wherein the perfume raw material comprises at least about 10% by weight of the perfume.

\* \* \* \* \*